United States Patent

Bellin et al.

Patent Number: 5,448,996
Date of Patent: Sep. 12, 1995

[54] PATIENT MONITOR SHEETS

[75] Inventors: Howard T. Bellin, New York; Robert P. Dingwall, Clinton Corners, both of N.Y.

[73] Assignee: Lifesigns, Inc., New York, N.Y.

[21] Appl. No.: 193,698

[22] Filed: Feb. 8, 1994

Related U.S. Application Data

[63] Continuation-in-part of Ser. No. 97,941, Jul. 26, 1993, abandoned, which is a continuation of Ser. No. 474,355, Feb. 2, 1990, abandoned.

[51] Int. Cl.$^6$ .............................. A61B 5/0205
[52] U.S. Cl. ................... 128/671; 128/721; 128/782
[58] Field of Search ............... 128/670–671, 128/721–723, 715, 774, 782

[56] References Cited

U.S. PATENT DOCUMENTS

| | | | |
|---|---|---|---|
| Re. 32,180 | 6/1986 | Lewiner et al. | 340/573 |
| 4,308,870 | 1/1982 | Arkans | 128/640 |
| 4,509,527 | 4/1985 | Fraden | 128/671 |
| 4,572,197 | 2/1986 | Moore et al. | |
| 4,576,179 | 3/1986 | Manus et al. | 128/671 |
| 4,738,264 | 4/1988 | Orlando | 128/671 |
| 4,909,260 | 3/1990 | Salem et al. | 128/721 |
| 4,960,118 | 10/1990 | Pennock | 128/721 X |
| 5,125,412 | 6/1992 | Thornton | 128/671 X |
| 5,271,412 | 12/1993 | Shtalryd et al. | 128/721 |

Primary Examiner—Angela D. Sykes
Attorney, Agent, or Firm—Hopgood, Calimafde, Kalil & Judlowe

[57] ABSTRACT

A patient monitor sheet device of simplified construction permits the accurate measurement of respiration, heart beat, and body position with a minimum of intrusion on the subject. Sensors are located in a bed sheet with which a subject comes in contact. One sensor produces a signal corresponding to respiratory induced, pulmonary motion, and myocardial pumping sounds. A second sensor produces a signal corresponding to changes in body position. A processor amplifies and filters the induced signals resulting in resolved output highly correlated to respiration rate, heart beat rate, and changes in body position.

18 Claims, 4 Drawing Sheets

PATIENT MONITOR SHEETS

This is a continuation-in-part of prior, application U.S. Ser. No. 08/097,941 filed Jul. 26, 1993, now abandoned, which is a continuation of U.S. Ser. No. 07/474,355 filed Feb. 2, 1990, now abandoned.

FIELD OF THE INVENTION

This invention generally relates to electronic devices for monitoring bed-ridden individuals. More specifically, this invention relates to a system and apparatus capable of distinguishing and monitoring the position, respiration rate, and heart rate of a person on a bed using selective, integrated signal processing.

BACKGROUND OF THE INVENTION

Respiration and heart rate are two of several core functions critical to continued biological activity. They are, therefore, monitored, along with blood pressure, as key indicators of patient vitality. For example, most emergency rooms and intensive care wards are elaborately equipped with sophisticated equipment for monitoring heart and lung function. Such monitoring is considered essential for the short and long term care of the patient.

Additionally, a patient's position on a bed also requires monitoring, especially during sleep. Monitoring is required to ensure avoidance of injury and liability that can result from a fall off the bed. This is especially true in cases where it is not essential that the patient be tied down with protective restraints or have side guards raised, both of these commonly used methods being restrictive and inconvenient. The current method is for hospital staff to make several, labor-intensive rounds per shift, checking on bed position.

The importance of heart and respiratory rate, and bed position in health care has made it desirable to monitor such functions outside the confines of the hospital and absent expensive hardware or professional help. In this regard, significant developments in sensor technology have led to inexpensive and portable heart monitors, often the size of a wristwatch. Blood pressure monitors have likewise enjoyed popularity due to simplified "home use" designs which have now become quite inexpensive. Such broadened application of these health sensors increases patient understanding of health problems and provides an early warning to potentially catastrophic events.

A demand exists for a simplified, inexpensive, but accurate device which can monitor heart rate, respiratory activity and bed-position. This is especially relevant for outpatients recently discharged from hospitals or patients requiring long term maintenance outside expensive medical facilities. Such patients require a simple, uncomplicated monitor, which monitor requires minimum attendance by a caretaker. Such monitors would be used to track basal heart and respiratory rate and give a warning indication if abnormal heart rate or breathing difficulties are noted on a continuous basis. Prompt detection of respiratory or cardiac anomaly would allow time for correction or early resuscitation. Similarly, a caretaker can prevent unwanted falls from a bed if given proper early warning detected from monitoring a patient's position on the bed.

SUMMARY AND OBJECTS OF THE INVENTION

It is an object of the present invention to provide a device for monitoring heart rate, respiratory activity and bed-position in a subject.

It is an additional object of the present invention to provide a system for tracking respiratory induced motion and develop, by selective processing, a signal highly correlated to respiratory activity.

It is another object of the present invention to provide a system for tracking myocardial activity and develop, by selective processing, a signal highly correlated to heart rate.

Another object of the present invention is to provide a system for monitoring bed position of a patient and develop, by selective processing, a signal highly correlated to the position of the patient on the bed.

It is a further object of the present invention to provide a device comprising a sensor and a data processor, wherein the sensor measures respiratory induced motion and heart beat, and generates an electrical signal containing frequencies associated with said motion and said beat; and the data processor receives the electrical signal and segregates it into highly correlated measurements of respiratory rate and heart rate.

Yet another object of the present invention to provide a device comprising a sensor and a data processor, wherein the sensor monitors patient bed position, and generates an electrical signal correlating with said bed position; and the data processor receives the electrical signal and generates perceptible data of the patient's position in bed.

The above and other objects of the present invention are realized in a specific illustrative patient monitor sheet device. The patient monitor sheet device comprises a monitor sheet, a signal processor segment, and a digital output system which may be connected to a display, a recording or an alarm control system, or a combination thereof.

In the preferred embodiment, the monitor sheet comprises an assembly of consequtive bonded layers made up of at least three plastic sheets with a piezo-electric film between the bottom two plastic sheets and foil between the top two plastic sheets. The foil and the piezo-electric film each comprise a sensor segment.

As the subject comes in contact with the patient monitor sheet, the sensors flex in response to body position, heart beat, and respiration, causing the piezo-electric films to bend, thereby producing output signals, and the combination of the subject's body, plastic sheet and foil layer create a capacitor at points of contact with the subject and produces another output signal. A processor receives the output signals, amplifies them, and resolves the body position, heart beat, and respiratory induced portion of the signal from each other, from background noise, and from other artifacts. The processor outputs a resolved signal for digital output or control of alarms.

Modifications to this exemplary embodiment described summarily above would be obvious to those skilled in the art. For instance, for those only desiring a patient body position monitor, the monitor sheet comprises an assembly of at least two plastic sheets with a layer of foil therebetween. The foil comprises a sensor segment. As the subject comes in contact with the patient monitor sheet, the combination of the subject's body, plastic sheet and foil layer create a capacitor at points of contact with the subject and produces an output signal which is resolved to signals for digital output or control of alarms.

BRIEF DESCRIPTION OF THE DRAWINGS

The foregoing features of the present invention can be more fully understood from the following detailed discussion of a specific illustrative embodiment thereof, presented hereinbelow in conjunction with the accompanying drawings, in which.

DETAILED DESCRIPTION OF THE PREFERRED EMBODIMENT

Figure 1:
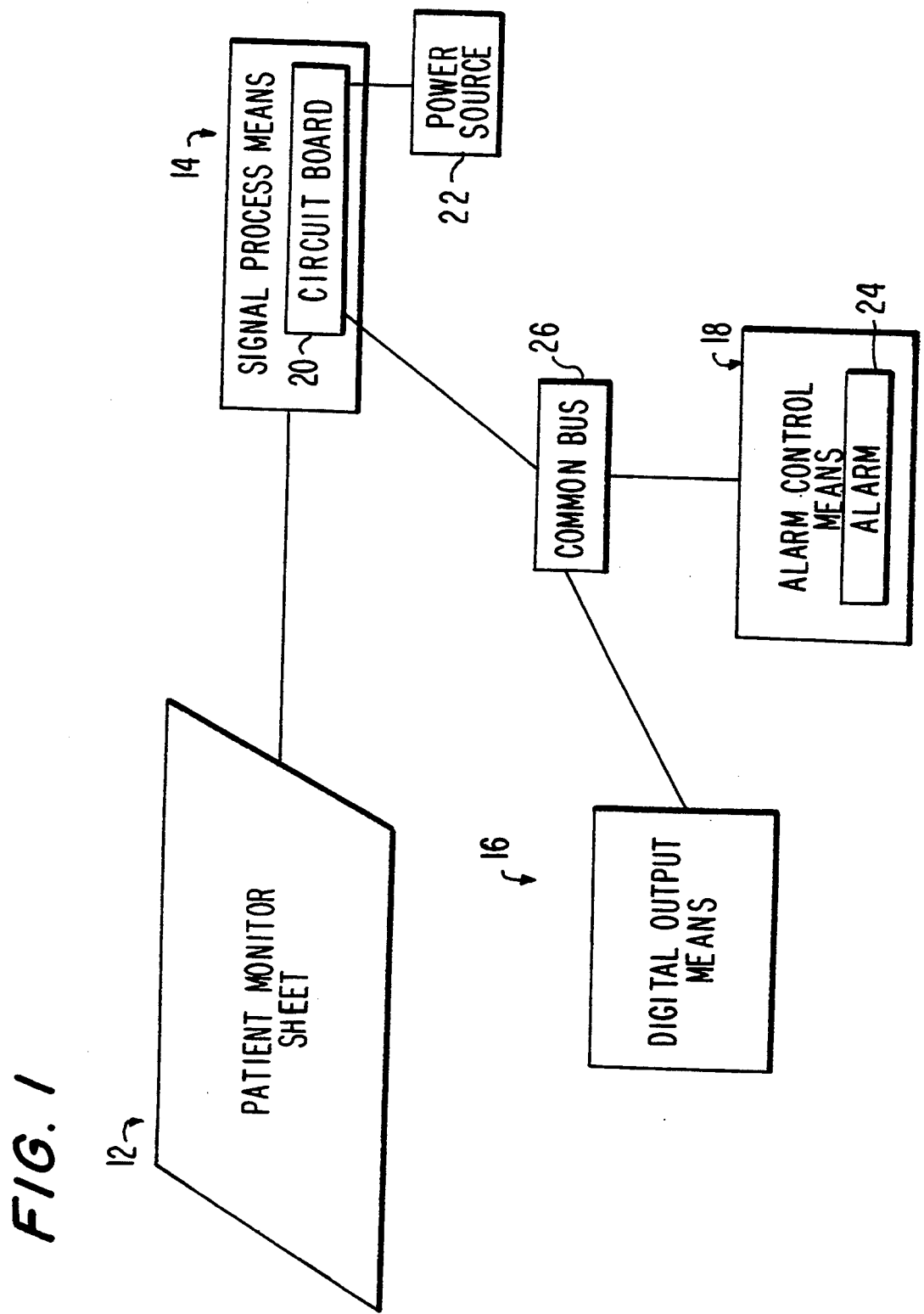
FIG. 1 is a schematic overview of the patient monitor system.

FIG. 1 shows a schematic representation of the general components of the present patient monitor device. More particularly, the patient monitor device comprises a monitor sheet 12 connected to a signal processor means 14, which in turn is connected to a digital output means 16 or to an alarm control means 18.

The signal processor means 14 comprises a circuit board 20 connected to a power supply 22. The circuit board 20 incorporates a system-controlling, stored program. The output of circuit board 20 can connect to the digital output means 16 or the alarm control means 18 by a common bus 26. The power supply 22 is preferably an AC adaptor. The digital output means 16 preferably comprises a liquid crystal display ("LCD"). The digital output means 16 is a digital display of the output of current body position, heart beat, and/or respiration rate. The digital output means 16 also provides the display of various system modes of operation, as will be more fully explained below.

The signal processor means 14 is connected to the alarm control means incorporating an audible alarm 24. Alternatively, a receiver and alarm can be located remotely from the monitor, thus permitting distant monitoring of respiration up to the range limits of a suitable telemetry transmitter used.

Figure 2:
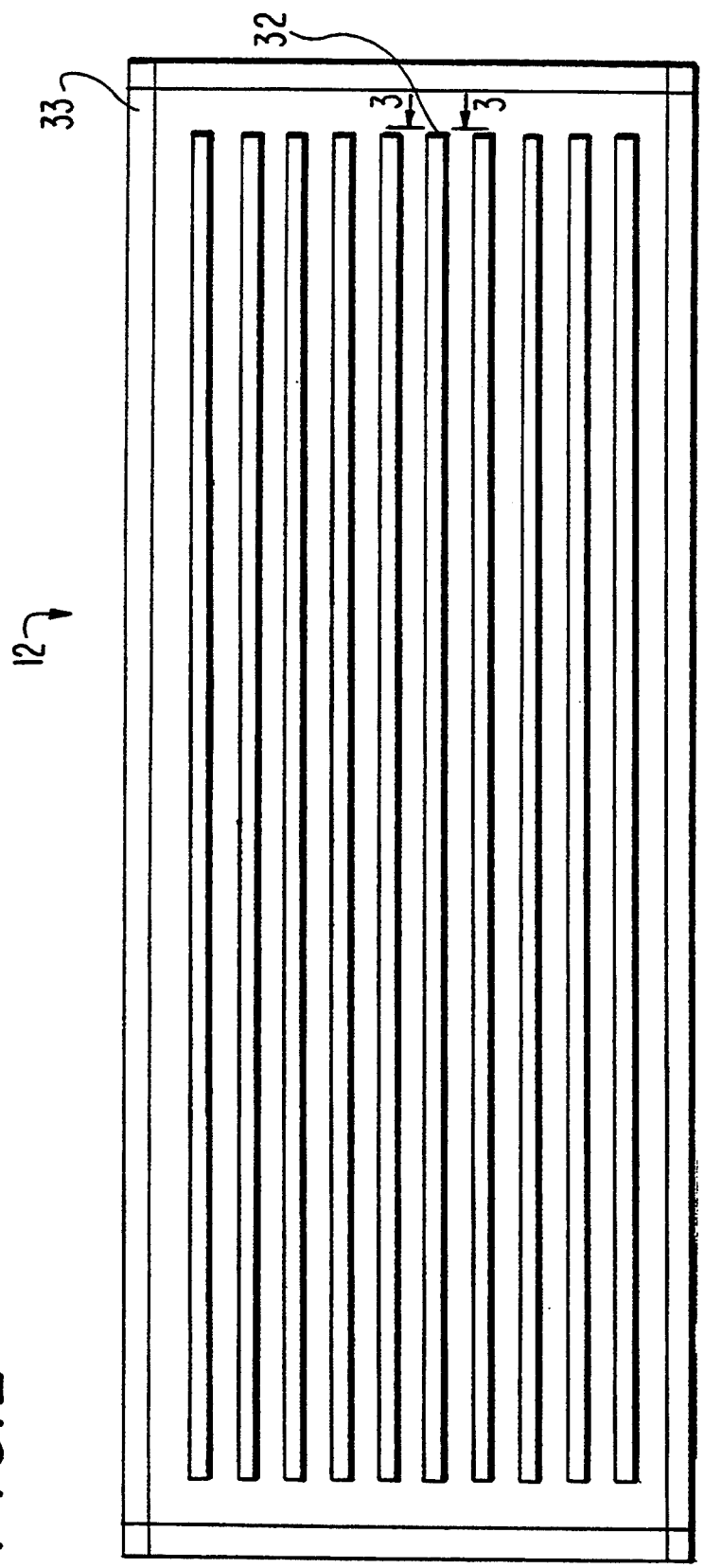
FIG. 2 is a diagramatic, plan view of the monitor sheet.

Continuing with FIG. 2, a diagramatic, plan view of the monitor sheet 12 is shown depicting parallel, longitudinal strips incorporated therein. Monitor strip 32 is representative of one of such multiple parallel longitudinal strips. Side strip 33 is also depicted forming a rectangular edge on the perimeter of sheet 12. Side strip 33 is designed to overhang a bed such that a limb overhanging the edge of the bed can be detected and give an early indication that the rest of the monitored patient's body is imminently going to be displaced out of the bed.

The monitor strips need not be longitudinal, nor in parallel arrangement as depicted in FIG. 2. The "strips" may also take on a variety of geometric shapes, such as circles or squares, and can be placed in any suitable arrangement on monitor sheet 12.

Figure 3:
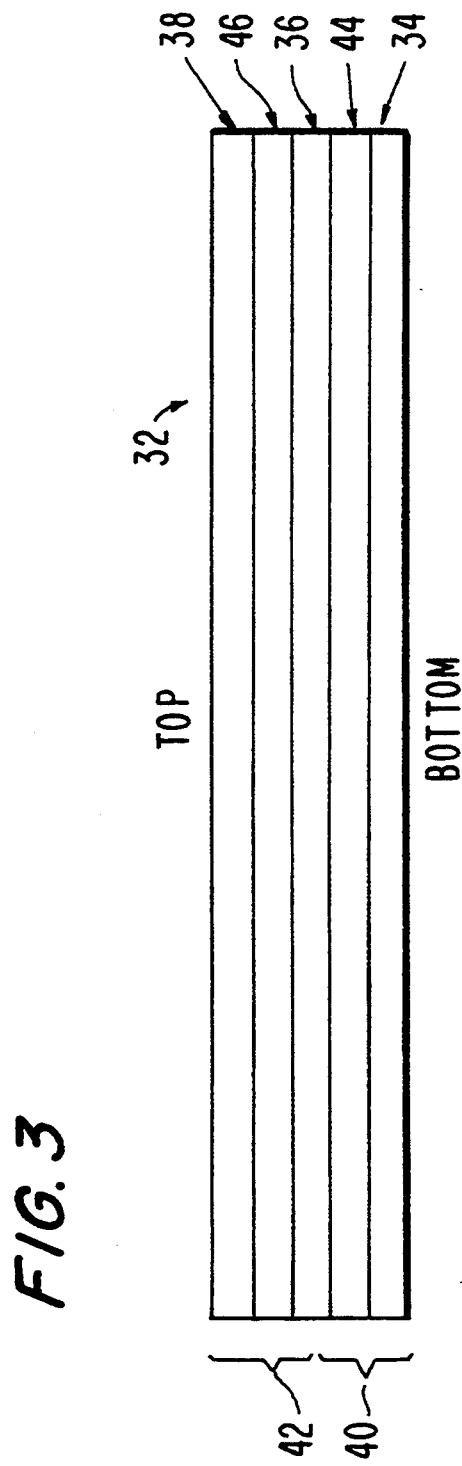
FIG. 3 is a cross-sectional, diagramatic view of a monitor strip taken along lines 3—3 of FIG. 2.

FIG. 3 is a cross-sectional, diagramatic view of monitor strip 32 taken from FIG. 2 along lines 3—3. The monitor strip 32 comprises an assembly of consequtively superimposed adhering layers made up of a bottom plastic sheet 34, a middle plastic sheet 36, and a top plastic sheet 38. A lower sensor segment 40 is thereby created between the bottom plastic sheet 34 and the middle plastic sheet 36, and an upper sensor segment 42 is similarly created between the middle plastic sheet 36 and the top plastic sheet 38. Although the general term "plastic" is described for the sheet material, one skilled in the art could easily substitute any flexible polymeric material capable of deformation for such sheets.

The lower sensor segment 40 is comprised of a relatively flat, piezo-electric film 44 (which is electrically connected via common bus 26 to the signal processor means 14, see FIG. 1). The upper sensor segment 42 is comprised of a layer of aluminum foil 46, electrically connected via common bus 26 to the signal processor means 14 (see also FIG. 1).

Referring back to FIG. 3, the lower sensor segment 40 comprised of flexible polymeric material, plastic sheets 34 and 36, and piezo-electric film 44, is capable of deformation in response to respiratory induced motion and also picks up myocardial activity representing heart beat. The upper sensor segment 42, comprised of flexible polymeric material, plastic sheets 36 and 38, and flexible metal, foil 46, is capable of deformation in response to changes in limbs, head and torso of the patient, representing body position. Each of sensor segments 40 and 42 is also electrically insulated, thereby protected from extraneous, noise inducing currents.

Referring back to FIG. 2, side strip 33 forming the rectangular edge of monitor sheet 12 may comprise only foil (without the piezo-electric film) for detecting body position only, such as, again, a subject about to fall out of bed.

Figure 4:
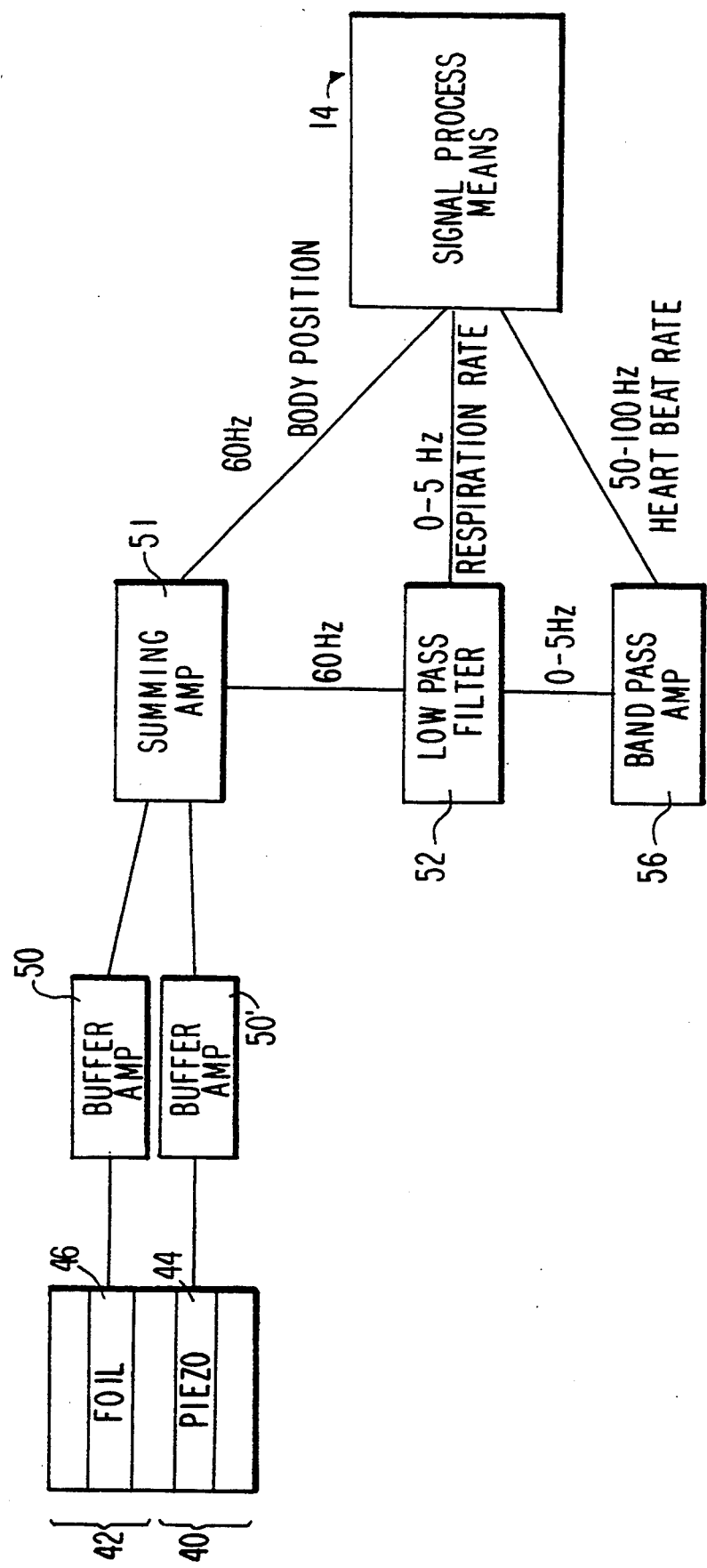
FIG. 4 is a schematic diagram of the signal processing.

Referring now to FIG. 4, a block diagram is shown depicting the operation of the signal processor means 14 with reference to input signals from lower sensor segment 40 (piezoelectric film 44) and upper sensor segment 42 (foil 46). More particularly, as the foil 46 undergoes bending forces in response to the weight of the body of the patient (not shown) the combination of the plastic layers 36 and 38 and foil 46 creates capacitance which provides an analog signal to buffer amplifier 50, which amplifier boosts the analog signal. The boosted signal is relayed to summing amplifier 51.

Meanwhile, the piezo-electric film 44 undergoes a bending force in response to pulmonary movement as the subject breathes, and also picks up myocardial pumping sounds as the heart circulates blood in the subject. The piezo film 44 generates an electrical current in response to such stimuli, and the current is amplified by buffer amplifier 50'. Buffer amplifier 50' then relays the boosted current to summing amplifier 51.

The output of summing amplifier 51 is set, for example, at 60 Hz. This signal is processed in signal processor 14 per parameters set in the program memory in circuit board 20 (see FIG. 1) to produce perceptible information as to body position and set off an alarm if required, by said parameters.

Simultaneously, the 60 Hz output signal is also filtered by lowpass filter 52 for the frequency range of 0–5 Hz which contains both frequencies corresponding to analog signals from respiratory motion and heart beat. Normal respiratory rate is 20 breaths per minute which is at about 1 Hz, maximum heart rate is set at about 120 beats per minute at about 5 Hz, while normal heart rate is about 72 beats per minute. Thus, the 5 Hz cut-off includes the desired frequency ranges.

The 0–5 Hz filtered signal is processed in signal processor 14 per parameters also set in program memory in circuit board 20 (see FIG. 1) to produce perceptible information as to respiratory rate and set off an alarm if required by said parameters.

Monitoring heart beat requires more sensitive processing when compared to respiratory motion. In a relative sense, the movement of the pulmonary cavity in response to the diaphragm is quite pronounced and piezo film 44 actually undergoes a bending force in response to the pulmonary movement of the subject which produces the desired analog signal for respiratory rate. The beating of the heart is not so pronounced and its signal requires some amplification after filtration. Thus, the filtered signal is further boosted in bandpass amplifier 56 to 50–100 Hz to be processed in signal processor 14 per parameters also set in program memory in circuit board 20 (see FIG. 1) to produce perceptible information as to heart rate and set off an alarm if required by said parameters.

The above-described arrangement is merely illustrative of the principles of the present invention. Numerous modifications and adaptations thereof will be readily apparent to those of ordinary skill in this art without departing from the spirit and scope of the present invention.

What is claimed is:

1. A device for monitoring patients, comprising:
  a) a sheet having a first sensor segment and a second sensor segment;
  b) said first sensor segment comprised of a metallic foil layer and a first flexible polymeric layer;
  c) said second sensor segment comprised of a piezo-electric film layer and a second flexible polymeric layer;
  d) said first sensor segment capable of generating an electrical signal corresponding to body position of said patient being monitored; and
  e) said second sensor segment capable of generating an electrical signal corresponding to respiratory induced, pulmonary motion and cardiovascular pumping action.

2. The monitoring device of claim 1, wherein said first sensor segment comprised of said metallic foil layer and said first flexible polymeric layer creates electric capacitance when a part of the body of said patient being monitored exerts a weight force thereon.

3. The monitoring device of claim 1, wherein said electric signal from said first sensor segment is filtered then processed in a signal process means capable of generating a digital output corresponding to body position of said patient being monitored.

4. The monitoring device of claim 1, wherein said electric signal from said second sensor segment is filtered then processed in a signal process means capable of generating a digital output corresponding to respiration rate and heart rate of said patient being monitored.

5. The monitoring device of claim 1, wherein said electric signal from said first sensor segment is processed in a signal process means having stored program memory containing parameters which sets off an alarm when the body position of said patient being monitored exceeds said parameters.

6. The monitoring device of claim 1, wherein said electric signal from said second sensor segment is processed in a signal process means having stored program memory containing parameters which sets off an alarm when the respiratory rate of said patient being monitored exceeds or falls below said parameters.

7. The monitoring device of claim 1, wherein said electric signal from said second sensor segment is processed in a signal process means having stored program memory containing parameters which sets off an alarm when the heart beat rate of said patient being monitored exceeds or falls below said parameters.

8. A patient monitoring sheet, comprising:
  a) a first sensor segment comprised of a layer of aluminum foil situated between a first flexible polymeric layer and a second flexible polymeric layer;
  b) a second sensor segment comprised of a piezo-electric film layer situated between said second flexible polymeric layer and a third flexible polymeric layer;
  c) said first sensor segment capable of generating an electrical signal corresponding to body position of said patient being monitored; and
  d) said second sensor segment capable of generating an electrical signal corresponding to respiratory induced, pulmonary motion and cardiovascular pumping action.

9. The monitoring device of claim 8, wherein said electric signal from said first sensor segment is filtered then processed in a signal process means capable of generating a digital output corresponding to body position of said patient being monitored.

10. The monitoring device of claim 8, wherein said electric signal from said second sensor segment is filtered then processed in a signal process means capable of generating a digital output corresponding to respiration rate of said patient being monitored.

11. The monitoring device of claim 8, wherein said electric signal from said second sensor segment is filtered then processed in a signal process means capable of generating a digital output corresponding to heart rate of said patient being monitored.

12. A device for monitoring respiratory activity, heart rate and body position, comprising:
  a) a first detector means sensitive to respiratory induced motion and heart beat sounds, said first detector means capable of generating a first electrical signal in response to said respiratory induced motion and heart beat;
  b) a second detector means sensitive to changes in body position, said detector means capable of generating a second electrical signal corresponding to movement by the detector means in response to said body position changes; and
  c) a processor means for receiving said first and second electrical signals from said detector means and converting said electrical signal into filtered signals for an output device.

13. The device of claim 12, wherein said first detector means comprises a piezo-electric film.

14. The device of claim 12, wherein said second detector means comprises a planar sheet of aluminum foil.

15. The device of claim 12, wherein said processor means comprises a signal amplifier coupled to at least one electronic filter.

16. The device of claim 15, wherein said filter is selected from the group consisting of those with a frequency cutoff of 5 Hz, 50 Hz, and 100 Hz.

17. The device of claim 12, wherein an alarm in communication with said processor means is triggered by a change in said respiratory induced motion or heart beat.

18. The device of claim 12, wherein an alarm in communication with said processor means is triggered by a change in said body position.

* * * * *